United States Patent [19]

Lutz et al.

[11] 4,124,639
[45] Nov. 7, 1978

[54] N-ALKOXYALKYL-2,6-DINITROANILINE HERBICIDES

[75] Inventors: Albert W. Lutz, Princeton; Robert E. Diehl, Lawrenceville, both of N.J.

[73] Assignee: America Cyanamid Company, Stamford, Conn.

[21] Appl. No.: 752,382

[22] Filed: Dec. 20, 1976

Related U.S. Application Data

[60] Continuation-in-part of Ser. No. 696,085, Jun. 14, 1976, abandoned, which is a continuation-in-part of Ser. No. 599,221, Jul. 25, 1975, abandoned, which is a division of Ser. No. 323,000, Jan. 12, 1973, Pat. No. 3,920,742, which is a continuation-in-part of Ser. No. 262,807, Jun. 14, 1972, abandoned, which is a continuation-in-part of Ser. No. 174,938, Aug. 25, 1971, abandoned.

[51] Int. Cl.$^2$ .......................... C07C 93/14; A01N 9/20
[52] U.S. Cl. ........................................ 260/573; 71/121
[58] Field of Search .................. 260/573, 577, 574; 71/121

[56] References Cited

U.S. PATENT DOCUMENTS

| 3,257,190 | 6/1966 | Soper | 260/574 X |
| 3,332,769 | 7/1967 | Soper | 71/121 |
| 3,726,923 | 4/1973 | Foster et al. | 260/577 |
| 3,764,624 | 10/1973 | Strong et al. | 260/574 |
| 3,849,107 | 11/1974 | Fischer | 71/121 X |
| 3,895,934 | 7/1975 | Linder et al. | 260/578 X |

FOREIGN PATENT DOCUMENTS 1,453,170  9/1966  France ..................... 260/577

Primary Examiner—Winston A. Douglas
Assistant Examiner—John J. Doll
Attorney, Agent, or Firm—H. G. Jackson

[57] ABSTRACT

The invention is substituted 2,6-dinitroaniline compounds and preemergence herbicidal methods and compositions employing the substituted 2,6-dinitroaniline compounds.

18 Claims, No Drawings

N-ALKOXYALKYL-2,6-DINITROANILINE HERBICIDES

This application is a continuation-in-part of copending application Ser. No. 696,085 filed June 14, 1976, now abandoned, which is a continuation-in-part Ser. No. 599,221 filed July 25, 1975, now abandoned, which is a division of Ser. No. 323,000 filed Jan. 12, 1973, now U.S. Pat. No. 3,920,742, which is a continuation-in-part of Ser. No. 262,807 filed June 14, 1972, now abandoned, which is in turn a continuation-in-part of application Ser. No. 174,938 filed Aug. 25, 1971, now abandoned.

The invention is substituted 2,6-dinitroaniline compounds and preemergence herbicidal methods and compositions employing the substituted 2,6-dinitroaniline compounds.

The 2,6-dinitroaniline compounds of the invention may be represented by the following structural formula:

[Structure I: benzene ring with $R_1R_2N$- at position 1, $O_2N$- at positions 2 and 6, Z at position 3, Y at position 4]

wherein,

Y is halogen, alkyl $C_1$–$C_4$, alkenyl $C_2$–$C_4$, or $CF_3$;

Z is alkyl $C_1$–$C_4$, alkenyl $C_2$–$C_4$, or mono-substituted alkyl $C_1$–$C_4$ where the substituent is halogen, alkoxy $C_1$–$C_4$ or —$NR_3R_4$;

$R_1$ is hydrogen, alkyl $C_1$–$C_6$, alkenyl $C_2$–$C_6$ or alkynyl $C_2$–$C_6$;

$R_2$ is mono-substituted alkyl $C_1$–$C_4$ where the substituent is alkoxy $C_1$–$C_4$; and $R_3$ and $R_4$ each are hydrogen or alkyl $C_1$–$C_4$.

Illustrative lower alkyl substituents are methyl, ethyl, n-propyl, iso-propyl, n-butyl, t-butyl, n-pentyl, n-hexyl, 2-pentyl, 3-pentyl, sec-butyl, and the like.

Illustrative loweralkenyl substituents are ethenyl, 1-propenyl, 2-propenyl, 1-butenyl, 2-butenyl, 3-butenyl, 1-pentenyl, 1-hexenyl, and the like.

Illustrative lower alkynyl substituents are ethynyl, 1-propynyl, 2-propynyl, 1-butynyl, 2-butynyl, 3-butynyl, 1-pentynyl, 1-hexynyl, and the like.

Illustrative halogen substituents are fluoro, chloro, bromo and iodo groups.

The above-identified compounds are highly effective herbicidal agents and particularly efficacious are those represented by the following formula:

[Structure II: benzene ring with H,R_2N- at position 1, $O_2N$- at positions 2 and 6, Z at position 3, Y at position 4]

wherein,

Y is $CH_3$, $C_2H_5$, i-$C_3H_7$, n-$C_3H_7$; i-$C_4H_9$, sec-$C_4H_9$ or Cl, $R_2$ is secondary $C_3$–$C_4$ alkyl monosubstituted with methoxy and Z is $CH_3$ or —$CH_2OCH_3$.

These compounds represent a preferred class of compounds within the above-broader generic class and show a marked superiority in herbicidal performance.

Wherein an asymmetric carbon atom exists in the dinitroaniline compounds above, optical isomerism may exist. Accordingly, such compounds may be employed as separate antimers or in admixture, as in a racemic composition. Unless there is indication to the contrary by reference to such a compound, the unresolved composition is intended herein. Separation of antimers, where desired, may be effected by conventional resolution techniques. A convenient method relates to the introduction of an optically active substituent, such as a (—)-sec-butylamino group into the ring system, as by nucleosubstitution, as exemplified below.

Preferably, application of these compounds, or active ingredients is made using the herbicidal compositions described below with conventional application methods.

The 2,6-dinitroaniline compounds are prepared by a nucleophilic substitution of a 1-substituent, such as, a chloro group, with the appropriately substituted amine. While chloro is a preferred substituent, and the discussion is in terms thereof other conventional equivalent substituents, such as, bromo or iodo are included herein. The displacement may be conducted with or without an organic solvent, such as toluene, benzene or preferably xylene.

The reaction, which is graphically illustrated below, is carried out by heating the reactants, preferably between 50° C. and 150° C.

[Reaction: Structure III (benzene with Cl at 1, $O_2N$ at 2 and 6, Z at 3, Y at 4) + $R_1R_2NH$ (V) → xylene/Δ → Structure IV (benzene with $R_1R_2N$ at 1, $O_2N$ at 2 and 6, Z at 3, Y at 4)]

For purposes of further discussion, the active ingredients may be considered as falling into one of four classes of compounds, labeled as Types A through D. In type A compounds, Y is alkyl $C_1$–$C_4$. In Type B compound, Y is alkenyl $C_2$–$C_4$. In Type C compounds, Y is halogen and preferably chlorine or bromine. In Type D compounds, Y is trifluoromethyl.

Type A compounds, where Y and Z are lower alkyl groups, can be prepared by reacting the appropriately substituted 2,6-dinitrochlorobenzene with the appropriate amine.

The chlorobenzene intermediates for Type A compounds can be prepared by reacting an appropriately substituted aniline with ethyl chloroformate in benzene at about 10° C. to 50° C. to yield the correspondingly substituted N-(ethoxycarbonyl)-3,4-substituted aniline. This product is then treated with a cold solution of sulfuric and nitric acid, i.e., at about 0° C. to 20° C. to obtain the N-(ethoxycarbonyl)-3,4-disubstituted-2,6-dinitroaniline. Reaction of the thus-formed product with sulfuric acid at an elevated temperature, preferably between about 100° C. and 150° C., converts the N-(ethoxycarbonyl) product to the 3,4-disubstituted-2,6-dinitroaniline. The amino group is replaced by a chlorine atom by first heating the compound with glacial acetic acid and diazotizing the amine with a mixture of sodium nitrite in sulfuric acid. This is followed by treating the diazotized mixture with a mixture of cuprous chloride in hydrochloric acid, and then heating the thus-formed mixture to about 40° C. to 80° C. to obtain the chlorinated compound.

Selected chlorinated intermediates for Type A compounds can also be prepared by reacting a mixture of fuming sulfuric acid and fuming nitric acid with 4-chloro-o-xylene at about 10° C. to 60° C., pouring the mixture over ice and separating the precipitated solid. Recrystallization of the solid from methanol or other lower alkyl alcohol $C_1$–$C_4$ yields the high purity product.

Illustrative Type A compounds which are readily prepared by the preceding procedure include, for example: 3,4-dimethyl-2,6-dinitro-N,N-di-n-propylaniline; N-ethyl-N-n-propyl-3,4-dimethyl-2,6-dinitroaniline; N,N-di-n-butyl-3,4-dimethyl-2,6-dinitroaniline; 3,4-dimethyl-2,6-dinitro-N-oxydiethyleneaniline; 3,4-dimethyl-2,6-dinitro-N-pentamethyleneaniline; 3,4-dimethyl-2,6-dinitro-N-tetramethyleneaniline; N,N-dicyclopropyl-3,4-dimethyl-2,6-dinitroaniline; N,N-diallyl-3,4-dimethyl-2,6-dinitroaniline; N-ethyl-N,3,4-trimethyl-2,6-dinitroaniline; N,3,4-trimethyl-2,6-dinitro-N-(cyclopropyl)aniline; N,N-dipropargyl-3,4-dimethyl-2,6-dinitroaniline; N,N-bis(1-buten-3-yl)-3,4-dimethyl-2,6-dinitroaniline; N-ethyl-3-isopropyl-4-methyl-2,6-dinitroaniline; 3-sec-butyl-4-methyl-2,6-dinitro-N,N-dimethylaniline; N,N,3,4-tetramethyl-2,6-dinitroaniline; N,N-diethyl-3,4-dimethyl-2,6-dinitroaniline; N,3,4-trimethyl-2,6-dinitro-N-propylaniline; N-cyclobutyl-N,3,4-trimethyl-2,6-dinitroaniline; 3,4-dimethyl-2,6-dinitro-N,N-(dicyclopropylmethyl)aniline; N,3,4-trimethyl-2,6-dinitroaniline; N-ethyl-3,4-dimethyl-2,6-dinitroaniline; 3,4-dimethyl-2,6-dinitro-N-(cyclopropyl)aniline; N-isopropyl-3,4-dimethyl-2,6-dinitroaniline; N-allyl-3,4-dimethyl-2,6-dinitroaniline; N-n-butyl-3,4-dimethyl-2,6-dinitroaniline; N-sec-butyl-3,4-dimethyl-2,6-dinitroaniline; and 3,4-dimethyl-2,6-dinitro-N-3-pentylaniline.

The 3,4-diethyl derivatives, 3-methyl-4-ethyl derivatives, 3-ethyl-4-methyl, 3-ethyl-4-propyl, 3,4-diisopropyl, 3,4-di-n-propyl, 3,4-di-n-butyl, 3,4-diisobutyl, 3-propyl-4-butyl, and 3-methyl-4-isopropyl derivatives of the above-named 2,6-dinitroanilines, are likewise prepared by the above procedure, utilizing the appropriate 3,4-disubstituted-2,6-dinitrochlorobenzene and appropriate amine.

Type B compounds, where Y represents a lower alkenyl $C_2$–$C_4$ group, are prepared by the procedure described above. The reaction is preferably run in xylene at a temperature between about 50° C. and 150° C. and involves the reaction of a 3-substituted-4-alkenyl-2,6-dinitrochlorobenzene with the appropriate amine. In this reaction, Z is preferably methyl or ethyl, although it may be any of the radicals previously described for it.

Illustrative Type B compounds, which can be prepared by this procedure include, for example: N-sec-butyl-4-isobutenyl-3-methyl-2,6-dinitroaniline; 4-isopropenyl-3-methyl-2,6-dinitro-N,N-di-n-propylaniline; N,3-di-methyl-2,6-dinitro-4-n-propenylaniline; and 4-isopropenyl-N,N,3,5-tetramethyl-2,6-dinitroaniline.

A preferred method for the preparation of Type C compounds wherein Y is halogen and Z is lower alkyl involves the reaction of a dihalo-dinitroalkylbenzene, such as 3,6-dihalo-2,4-dinitrotoluene, with the appropriate amine. The reaction is preferably carried out in the presence of an organic solvent, such as $C_1$–$C_4$ alcohols, toluene and the like. The reaction may be conducted at room temperature, although heating is generally advantageously employed.

Type D compounds can be prepared by reacting the appropriate 3-substituted-4-trifluoromethyl-2,6-dinitrochlorobenzene with the appropriate amine, preferably by heating the reactants in the presence of an organic solvent such as benzene, toluene or the like.

Preparation of chlorobenzene intermediates for use in this reaction are described by Newman and Pinkus, *Journal of Organic Chemistry* 19: 978, and Von Auwers and Julicker, *Chemische Berichte* 55: 2167 (1922). For example, 4-methylphenol may be treated with aluminum trichloride in carbon tetrachloride to obtain 2,6-cyclohexadien-1-one which is treated with phosphoruspentachloride to yield 3-methyl-4-trichloromethylchlorobenzene. When the latter compound is treated with $SbF_3$, 1-chloro-3-methyl-4-(trifluoromethyl)benzene is obtained. This product may be nitrated using a mixture of nitric acid and sulfuric acid to give the intermediate, 1-chloro-3-methyl-2,6-dinitro-4-(trifluoromethyl)benzene.

Illustrative Type D compounds which can be prepared by this process include, for example: 3-methyl-2,6-dinitro-N,N-di-n-propyl-4-(trifluoromethyl)aniline; N-sec-butyl-3-methyl-2,6-dinitro-4-(trifluoromethyl)aniline; 3-methyl-2,6-dinitro-N-3-pentyl-4-(trifluoromethyl)aniline; N-cyclopropyl-3-methyl-2,6-dinitro-4-(trifluoromethyl)aniline; and 3-ethyl-2,6-dinitro-N-isopropyl-4-(trifluoromethyl)aniline.

The preemergence herbicidal compositions of the present invention are solid or liquid formulations comprising an effective amount of one or more of the 2,6-dinitroaniline compounds of Formula I, or preferably Formula II, and those compounds corresponding to Formula I wherein $R_2$ also represents methyl with a herbicidal adjuvant, i.e., an inert carrier or other conventional formulation aid.

Preparation of the compositions broadly involves admixing an effective amount of the herbicidal agent and adjuvant.

Use of the compositions broadly involves application of an effective amount of the compounds or preferably the compositions to the soil containing seeds of the plants to be controlled.

Typical formulations include, for example, dusts, dust concentrates, wettable powders, granulars, and the like. Application by conventional methods and equipment is usually made at rates of from about ⅛ pound per acre to about 20 pounds per acre and preferably ¼ to 8 pounds per acre of active material.

Dusts are generally prepared by grinding together from about 1% to 15% by weight of the active material with from about 99% to 85% by weight of a solid diluent, such as an attaclay, kaolin, diatomaceous earth, fullers earth, talc, pumice or the like.

Dust concentrates are prepared in similar fashion to the dusts excepting that generally about 15% to about 95% by weight of active material is used.

Granular formulations may be prepared by applying a liquid solution of the active material to sorptive granular carriers, such as attaclay, kaolin, or diatomite granules. Alternatively, they may be mixed with inert carriers and applied to non-sorptive granules, such as sand or limestone.

Wettable powders are prepared by grinding the active ingredient with a solid carrier, such as used in the dust formulations. Usually, about 25% to 75% by weight of the active material and from about 73% to 23% by weight of solid carrier is used. In addition, there is generally added about 1% to 5% by weight of a dispersing agent, such as alkali metal salts of naphthalene sulfuric acid and anionic-nonionic blends, and from about 1% to 5% by weight of a surfactant, such as polyoxyethylene alcohols, acids, adducts, sorbitan fatty acid esters and sorbitol esters. Typical formulations by weight percent are given below.

TABLE I

| | Typical Wettable Power Formulations |
|---|---|
| A | Ingredients |
| 25% | 4-ethyl-α-methoxy-N-(2-methoxy-1-methylethyl)-2,6-dinitro-m-toluidine |
| 65% | attaclay |
| 5% | sodium lignosulfonate |
| 5% | sodium N-methyl-N-oleoyl taurate |
| B | Ingredients |
| 33% | 4-chloro-α-methoxy-N-(3-methoxy-1-methylpropyl)-2,6-dinitro-m-toluidine |
| 59% | attaclay |
| 5% | sodium lignosulfonate |
| 3% | alkyl phenoxy polyoxyethylene ethanol |
| C | Ingredients |
| 40% | 4-ethyl-α-methoxy-N-[1-(methoxymethyl)propyl]-2,6-dinitro-m-toluidine |
| 50% | precipitated hydrated silicon dioxide (Hi Sil)[a] |
| 5% | sodium lignosulfonate |
| 3% | anionic-nonionic blend (MAL-77L)[b] |
| 2% | wetting agent |

[a]By Pittsburgh Plate Glass Company
[b]By Wm. Cooper and Nephews

The wettable powder formulations are usually dispersed in water and applied as a liquid soray to the area or locus where control of undesirable plant species is desired.

For use as preemergence herbicides, the dusts or liquid sprays containing the active compound can be applied to the soil shortly after planting or they may be incorporated into the soil by the technique referred to as preplant incorporation.

The practice and advantages of the present invention and preparation of the active ingredients used therein is further illustrated by the following examples which are not to be taken as being limitative thereof. Parts and percentages herein are by weight unless otherwise indicated.

EXAMPLE 1

Preparation of 3,4-Dimethyl-2,6-dinitrochlorobenzene

Two grams of 3,4-dimethyl-2,6-dinitroaniline [*Chemical Abstracts* 44: 4447 (1950)] is dissolved in 40 ml. of warm glacial acetic acid. The solution is cooled to room temperature and a mixture of 0.9 grams of sodium nitrite in 7 ml. of concentrated sulfuric acid is added very slowly leaving a solid in the mixture. This mixture is then added to a solution of cuprous chloride in concentrated hydrochloric acid. The cuprous chloride solution is prepared by dissolving 3.24 grams of $CuSO_4.5H_2O$ in water and adding NaCl to the warm solution. While holding the blue solution in an ice bath, a solution of 1.24 grams of sodium meta-bisulfite and 0.52 grams of NaOH in 12 ml. of water is added. A white precipitate forms and is dissolved in 12 ml. of concentrated hydrochloric acid. The diazonium mixture is then warmed, filtered, and the solid collected and recrystallized from cyclohexane. The product has a melting point of 109° C. to 111° C. The procedures are repeated using 16 grams of the amine, yielding 11 grams of product, having a melting point of 111° C. to 113° C.

EXAMPLE 2

Preparation of 3,4-Dimethyl-2,6-dinitrochlorobenzene

Fuming sulfuric acid (750 ml., 23%) and fuming nitric acid (240 ml., 90%) are mixed at 0° C. to 45° C. Then 4-chloro-o-xylene (270 grams, 1.93 moles) is added at 10° C. to 60° C. When the addition is complete, the reaction mixture is poured into 8000 ml. of ice and 4000 ml. water and then filtered. The cake is washed with 4000 ml. of water, 500 ml. methanol, and finally 500 ml. of petroleum ether. The cake is then slurried two times with 200 ml. xylene and filtered. The filter cake is then washed with 50 ml. cold xylene and 300 ml. of methanol at 50° C. The solid is then recrystallized from 2500 ml. of methanol and washed with 2 pints of petroleum ether. The yield of white solid is 120 grams with melting point 112° C. to 113° C.

EXAMPLE 3

Preparation of 3,4-Dimethyl-2,6-dinitro-N,N-di-n-propylaniline

Five grams of 1-chloro-3,4-dimethyl-2,6-dinitrobenzene and 5.05 grams of di-n-propylamine are dissolved in benzene and the mixture is refluxed. The benzene is then removed from the mixture by boiling and toluene is added to the remaining residue. The thus-formed mixture is then refluxed, filtered, and the filtrate stripped in vacuo. The residue is treated with hexane and the mixture chilled in dry ice and acetone. The solid from the mixture is collected and dried, it has a melting point of 42° C. to 43.5° C. and is the desired product.

EXAMPLE 4

Preparation of N-Isopropyl-3,4-dimethyl-2,6-dinitroaniline

4-Chloro-3,5-dinitro-o-xylene (10.0 grams, 0.043 mole) and i-propylamine (10.1 grams, 0.17 mole) are mixed and refluxed for 12 hours using an efficient reflux condenser. The mixture is then cooled and poured into 100 ml. of 5% hydrochloric acid and extracted with diethyl ether. The ether extract is dried over magnesium sulfate. Removal of the drying agent and solvent leaves an orange oil which readily solidifies. The product is recrystallized from methanol to give 8.7 grams (80%) of an orange solid with melting point 69° C. to 70° C.

EXAMPLE 5

Preparation of N-sec-Butyl-3,4-dimethyl-2,6-dinitroaniline

A mixture of 4-chloro-3,5-dinitro-o-xylene (140 grams, 0.61 mole), mono-sec-butylamine (184 ml., 1.82 moles), and xylene (1400 ml.) is brought to reflux. After refluxing overnight, the reaction mixture is cooled and filtered. The precipitate is washed with petroleum ether. The filtrate and washings are combined, washed with 500 ml. of 10% hydrochloric acid, and finally with 2 liters of water. The organic layer is separated and dried. Removal of the drying agent and the solvent leaves an orange oil which crystallizes with the addition of petroleum ether. A yellow orange solid (150.6 grams, 86.5%) with melting point 42° C. to 43° C. is collected.

EXAMPLES 6 to 10

Following the general procedures of Examples 4 and 5, substituting the appropriate amine for the amines used therein, yields products having the following formula and properties set forth in Table II below.

TABLE II

| Example Number | Substituents | | Melting Point ° C. |
|---|---|---|---|
| | $R_1$ | $R_2$ | |
| 6 | H | CHCH$_2$OCH$_3$ with CH$_3$ branch | oil |
| 7 | H | CH$_2$CH(OCH$_3$)$_2$ | 72–73 |
| 8 | H | CH(C$_2$H$_5$)CH$_2$OCH$_3$ | 46–47.5 |
| 9 | H | CH(C$_2$H$_5$)CH$_2$OC$_2$H$_5$ | 47–49 |
| 10 | H | CH$_2$CH$_2$CH$_2$OCH$_3$ | 43–44 |

EXAMPLE 11

Preparation of N-(3-Hexyl)-4-allyl-3-methyl-2,6-dinitroaniline

One equivalent of 4-allyl-3-methyl-2,6-dinitrochlorobenzene is dissolved in three volumes of xylene containing two equivalents of 3-hexylamine. The mixture is refluxed for 5 hours and then poured into water. The organic phase is washed with 5% hydrochloric acid and then water, dried over calcium sulfate, and removed in vacuo to leave the above-named product.

EXAMPLE 12

Preparation of 4-Chloro-N-isopropyl-3-methyl-2,6-dinitroaniline

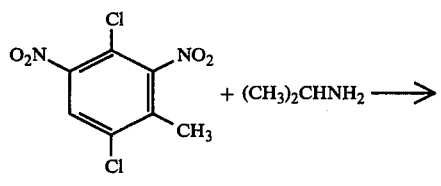

VI  VII

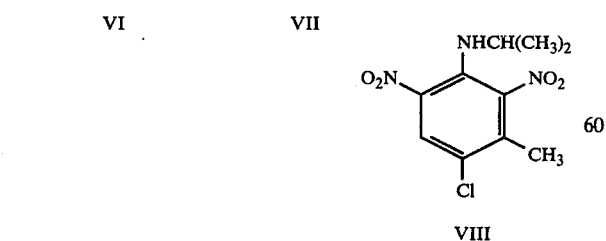

VIII

To a stirred mixture of 10.0 grams (0.04 mole) of 3,6-dichloro-2,4-dinitrotoluene in 50 ml. of ethanol is added 9.0 grams (0.15 mole) of isopropylamine. The mixture is stirred at room temperature for 2 hours and then at reflux for one hour. The solution is allowed to cool to room temperature and the crystalline precipitate is filtered and washed with a little hexane to give 10.2 grams of golden crystals, melting point 69° C. to 73° C. Two recrystallizations from methanol give the analytically pure compound, melting point 69° C. to 70° C.

EXAMPLE 13

Preparation of 4-Chloro-3-methyl-2,6-dinitro-N,N-dipropylaniline

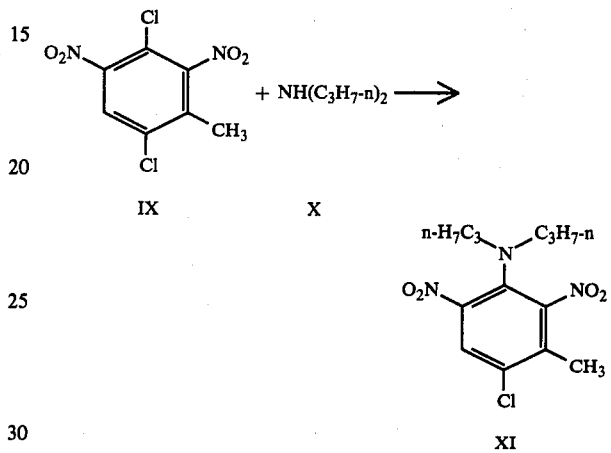

IX  X

XI

A solution of 10.04 grams (0.04 mole) of 3,6-dichloro-2,4-dinitrotoluene, 12.2 grams (0.12 mole) of di-n-propylamine, and 60 ml. of toluene is stirred at reflux for 9 hours. The mixture is cooled, diluted with ether, and extracted twice with dilute hydrochloric acid. The organic phase is then extracted consecutively with water, aqueous sodium bicarbonate, and brine and dried over magnesium sulfate. Evaporation of the solvent at reduced pressure gives 12.5 grams of an oil. Crystallization of the product from hexane gives 9.08 grams of yellow solid, melting point 36° C. to 38° C. The analytically pure compound, melting point 41° C. to 42° C., is obtained by recrystallization from 95% ethanol.

EXAMPLES 14 to 15

Following the general procedure of Example 7, substituting the appropriate amine for the di-n-propylamine used therein, yields compounds of the following structural formula having properties set forth in Table III below:

TABLE III

XII

| Example Number | Substituents | | Melting Point ° C. |
|---|---|---|---|
| | $R_1$ | $R_2$ | |
| 14 | H | CH$_2$CH$_2$CH$_2$OCH$_3$ | 42.5–46.5 |
| 15 | H | CH$_2$CH$_2$CH$_2$OCH$_3$ | 43–47 |

EXAMPLE 16

Preparation of N-sec-Butyl-3-methyl-2,6-dinitro-4-(trifluoromethyl)aniline

A nitration mixture, consisting of 16.1 ml. of $H_2SO_4$ (d 1.84) and 1.9 ml. of $HNO_3$ (d 1.5), is heated to 55° C. and 3.5 grams of 5-chloro-2-(trifluoromethyl)toluene is slowly added. The mixture is heated for one hour at 55° C. followed by one hour at 110° C. The reaction mixture is cooled and poured onto ice to give 5-chloro-2-(trifluoromethyl)-4,5-dinitrotoluene as a cream-colored solid. The product is crystallized from cyclohexane to give 3.6 grams of cream-colored crystals, melting point 81° C. to 82° C. 1.8 Grams of 5-chloro-2-(trifluoromethyl)-4,6-dinitrotoluene is refluxed for 15 minutes with 3 ml. of mono-sec-butylamine and 30 ml. of benzene, cooled, filtered, washed with water until neutral, dried and vacuum stripped to give 1.5 grams of N-sec-butyl-3-methyl-2,6-dinitro-4-(trifluoromethyl)aniline as a yellow solid, melting point 38° C. to 39° C.

EXAMPLE 17

Preparation of (−)-N-[1-(Methoxymethyl)propyl]-2,6-dinitro-3,4-xylidine (−)-2-Amino-1-butanol [100 grams, prepared according to D. Pitre and E. B. Grabitz, Chimia 23, 399 (1969)] was added in a dropwise manner to a stirred solution of tert-butanol (800 ml.) containing potassium tert-butoxide (126 grams). After warming this mixture to 70° C. to 80° C. for 2 hours, methyl iodide (175 grams) was added slowly at temperatures below 50° C. The suspension which formed was then stirred with refluxing overnight. After removal of the solid phase by filtration, the filtrate was fractionally distilled to give (−)-1-(methoxymethyl)propylamine contaminated with traces of tert-butanol, boiling point 125° C. to 147° C./760 mm. This amine was then allowed to react with 4-chloro-3,5-dinitro-o-xylene, as described earlier, to give the desired product as a bright yellow solid with melting point 42.5° C. to 44° C., $[\alpha]_D^{25°} = -137.6°$ (c 2.504, chloroform).

EXAMPLES 18 to 19

The following optical isomers were also prepared using the appropriate optically active amine and following essentially the procedure of Example 17 above:

TABLE IV

| Example Number | Compound Name | Melting Point | 25° D |
|---|---|---|---|
| 18 | (+)-N-[1-(methoxymethyl)-propyl]-2,6-dinitro 3,4-xylidine | 43-44 | +132.2 (c 2.504, chloroform) |
| 19 | (−)-4-chloro-N-[1-methoxymethyl)-propyl]-2,6-dinitro-m-toluidine | 40-42 | −107 (c 2.466, $CHCl_3$) |

EXAMPLE 20

Preparation of $\alpha^3$-methoxy-N-(2-methoxy-1-methylethyl)-3,4-Xylidine

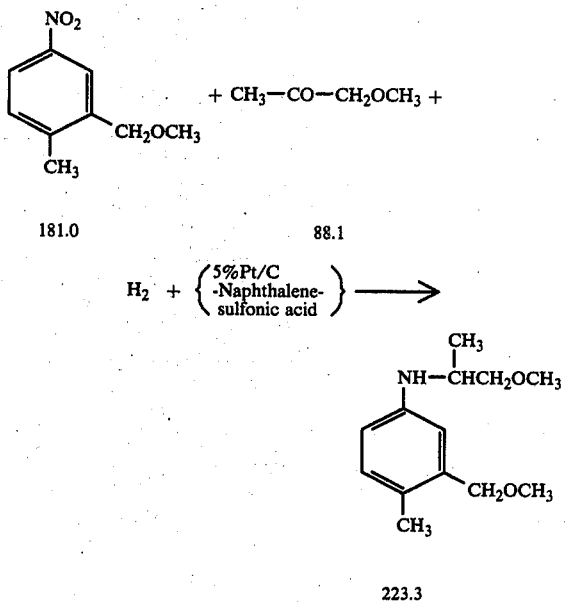

A mixture of methyl 2-methyl-5-nitrobenzyl ether (12 g, 0.066M), methoxyacetone [20 g (used as solvent)], 2-naphthalenesulfonic acid (0.3 g) and 5% Pt/C (0.7 g) is shaken on a Parr hydrogenator maintaining the temperature below 40° with external cooling. The theoretical amount of hydrogen (0.26M) is consumed and further uptake ceases after 2 hours.

The reaction mixture is filtered and the excess methoxyacetone removed in vacuo to yield a red oil. This oil is purified on a silica gel column, eluting with benzene, yielding 7.6 g (52%) of a colorless oil. Analysis calculated: C-69.91%; H-9.48%; N-6.26%; Found: C-69.88%; H-9.19%; N-6.36%.

EXAMPLE 21

Preparation of $\alpha^3$-Methoxy-N-(2-Methoxy-1-Methylethyl)-2,6-dinitro-3,4-Xylidene

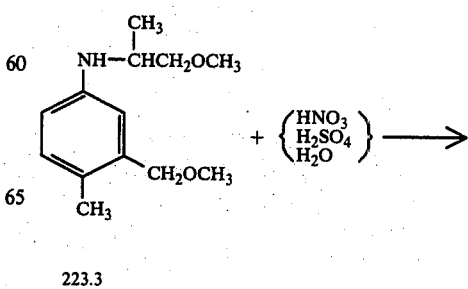

-continued-

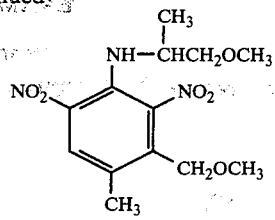

313.3

A nitration mixture consisting of conc. sulfuric acid (1.4 g), water (0.7 g) and 70% nitric acid (1.8 g) is added at 25° to a solution of $\alpha^3$-methoxy-N-(2-methoxy-1-methylethyl)-3, 4-xylidine (1.0 g, 0.004M) in 10 ml of dichloroethane. After stirring at 25° for 1 hour, then at 40° for 1 hour, the reaction mixture is cooled and poured onto ice. The desired product is obtained by extraction with chloroform and isolated as an orange oil, which is purified using a silica gel column, eluting with hexane/benzene (90/10). The resulting solid is crystallized from a small amount of methanol yielding 0.8 g. (64%) of light yellow crystals melting at 54.5°–56°. Analysis calculated: C-49.83%; H-6.11%; N-13.41%; Found: C-49.77%; H-5.90%; N-13.24%.

In a similar manner to Examples 20 and 21 the appropriate $\alpha$3-methoxy-3,4-xylidine or 4-chloro-$\alpha$-methoxy-m-toluidine is nitrated to give the following compounds:

| Ex | $R_2$ | Y | mp° C |
|----|-------|---|-------|
| 22 | CH(CH$_3$)CH$_2$OCH$_3$ | C$_3$H$_7$i | Orange oil |
| 23 | CH(CH$_3$)CH$_2$CH$_2$OCH$_3$ | C$_3$H$_7$i | Orange oil |
| 24 | CH(CH$_3$)CH$_2$CH$_2$OCH$_3$ | Cl | Orange oil |
| 25 | CH(CH$_3$)CH$_2$OCH$_3$ | Cl | 31–34 |

EXAMPLE 26

Preparation of $\alpha$-Chloro-2-ethyl-5-nitrotoluene

Paraformaldehyde (105.1g) was added portionwise to a stirred solution of 620 ml. of concentrated sulfuric acid and 720 ml. of fuming sulfuric acid at 3° C. to 10° C. Anhydrous calcium chloride (252.5g) was then added portionwise maintaining the temperature of the mixture between 4° C. and 11° C. The mixture was stirred in an ice bath for 1.5 hr. and then treated dropwise with 264.0g of 4-ethylnitrobenzene to maintain the reaction temperature between 6° C. and 9° C. The mixture was stirred between 9° C. and 18° C. for 13 hr. and then between 18° C. and 20° C. for 123 hr. The mixture was poured into a slurry of ice and water and the crude product was extracted with chloroform. The chloroform layer was partially concentrated, shaken with 100 ml. of potassium bicarbonate, water, and stirred over magnesium sulfate. The filtered solution was concentrated under vacuum to yield 317.6g of an amber liquid. The crude product was fractionated by vacuum distillation to yield a light yellow liquid with boiling point 114° C. to 118° C. at 0.2 mm. Hg.

Preparation of 2-Ethyl-5-nitrobenzyl methyl ether

Sodium methoxide 44.7g was added portionwise to a solution of 150.0g of $\alpha$-chloro-2-ethyl-5-nitrotoluene in 1.15l. of methanol maintained between 18° C. and 30° C. The mixture was refluxed for 2 hr., cooled to 3° C., and filtered. The filtrate was concentrated under vacuum and the resulting slurry shaken with saturated aqueous sodium chloride and methylene chloride. The methylene chloride layer was washed, filtered through sodium sulfate, and stirred over magnesium sulfate. The filtered solution was concentrated under vacuum to yield 133.89g of a dark brown liquid. The crude product was fractionated by vacuum distillation to yield a yellow liquid with boiling point 113° C. to 115° C. at 0.35 mm. Hg. which solidified to light yellow prisms with mp 21.5° C. to 23.5° C.

Preparation of 4-Ethyl-N-(1-ethylpropyl)-$\alpha$-methoxy-m-toluidine

A mixture of 10.0g of 2-ethyl-5-nitrobenzyl methyl ether, 10.38g of 3-pentanone, 0.23g of 2-naphthalene sulfonic acid, and 0.60g of 5% platinum on carbon catalyst was shaken under hydrogen for 2 hours at room temperature and for 4 hours at 48° C. to 60° C. The mixture was diluted with 200 ml of ether, filtered and the filtrate shaken with 2.5% aqueous sodium hydroxide, washed with water, filtered through sodium sulfate and stirred over magnesium sulfate. The filtered solution was concentrated under vacuum to yield 10.76 grams of an amber liquid, pure by glc and tlc analyses.

Preparation of 4-Ethyl-N-(1-ethylpropyl)-$\alpha$-methoxy-2,6-dinitro-m-toluidine A solution of 13.0g of concentrated nitric acid, 10.75 g of concentrated sulfuric acid, and 4.88 grams of water was added dropwise over a 2.3 hr. period to a stirred solution of 7.75 grams of 4-ethyl-N-(1-ethylpropyl)-$\alpha$-methoxy-m-toluidine in 35 ml. of 1,2-dichloroethane. The temperature of the mixture was maintained between 18° C. and 21° C. during the addition and for an additional 44 hr. The mixture was poured onto 30 g of ice and then extracted with methylene chloride. The extracts were combined with the dichloroethane layer, the combined organic layers washed with 2.5% aqueous sodium hydroxide and water and stirred over magnesium sulfate. The filtered solution was concentrated under vacuum to yield 10.86 g. of a dark brown solid. Purification by chromatography yielded yellow-orange crystals with m.p. 28° C. to 29° C.

4-Ethyl-$\alpha$-methoxy-2,6-dinitro-m-toluidine

The amine (100 g.) was slowly added to 2 l. of 50% sulfuric acid with stirring and then warmed to 70° C. for 22 hours. The reaction mixture was diluted with ice water, extracted with benzene and the benzene layer concentrated to an oily residue. The residue was taken up in CCl$_4$ (100 ml) and poured with stirring into hexane (1.2 l.). The resulting solid after drying weighed 74 g. (94% yield) and had m.p. 71°–73° C.

Preparation of 3-Chloro-6-ethyl-2,4-dinitrobenzyl methyl ether

A solution of the aniline (40 g. in 750 ml. acetic acid) was added slowly with stirring to a solution of NaNO$_2$ (17 g.) in 136 ml. sulfuric acid at 10°–15° C. After 30 minutes this reaction mixture was added to a solution of CuCl (37.8 g.) in 480 ml. hydrochloric acid with stirring. The product (25.0 g.) precipitated from the cooled reaction mixture in 58% yield with m.p. 81°–82°. The filtrate upon dilution yielded another 10 g. of product.

Preparation of 4-Ethyl-α-methoxy-N-[1-(methoxymethyl)propyl]-2,6-dinitro-m-toluidine The benzyl ether (5 g.) and 1-(methoxymethyl)-propylamine (4.1 g.) were dissolved in toluene (100 ml.) and heated to reflux. After 20 hours the reaction mixture was cooled, washed with dilute hydrochloric acid, water and then dried. After passing the solution through a column of neutral alumina, the toluene was removed in vacuo leaving 3.7 g. of an orange oil which upon standing crystallized. Recrystallization from methane gave the pure product, m.p. 54°–55° C.

In a similar manner using the appropriate benzyl ether and methoxyamine the following compounds are prepared.

| Ex | $R_2$ | Y | MP° C |
|---|---|---|---|
| 27 | $CH(CH_3)CH_2OCH_3$ | $C_2H_5$ | 62–64 |
| 28 | $CH(C_2H_5)CH_2OCH_3$ | $CH_3$ | 34.5–36.5 |
| 29 | $CH(C_2H_5)CH_2OCH_3$ | $C_3H_7$-i | red oil |

4-Ethyl-m-toluidine

α-Chloro-2-ethyl-5-nitrotoluene (40.0 g.) was dissolved in glacial acetic acid and shaken with 5% Pd/C in a hydrogen atmosphere (6.7 g.) in a Parr hydrogenator. When reduction was complete, the crude product was isolated, taken up in ether, washed with water, dilute base and water. After stirring the ether solution over solid $K_2CO_3$, the product was isolated as a liquid, 96% pure by glc.

4-Ethyl-N-(1-ethylpropyl)-m-toluidine

A mixture of 4-ethyl-m-toluidine (20.2 g.), 3-pentanone (38.7 g.), 2-naphthylsulfonic acid (0.7 g.) and 5% Pt/C (1.9 g.) was hydrogenated in a Parr apparatus. After removal of the catalyst, the filtrate was diluted with ether, washed with dilute base and water, dried, and stripped to give the product in 98% purity (glc).

4-Ethyl-N-(1-ethylpropyl)-2,6-dinitro-m-toluidine

The preceding m-toluidine was dinitrated in a manner similar to that used for 4-ethyl-N-(1-ethylpropyl)-α-methoxy-2,6-dinitro-m-toluidine to give the product after purification by chromatography with m.p. 51°–53°.

4-Ethyl-2,6-dinitro-m-toluidine

The above 2,6-dinitro-m-toluidine was dealkylated in a manner similar to that described for the preparation of 4-ethyl-α-methoxy-2,6-dinitro-m-toluidine. The desired product after recrystallization from hexane had m.p. 101°–101.5° C.

3-Chloro-6-ethyl-2,4-dinitrotoluene

The subject compound was prepared from 4-ethyl-2,6-dinitro-m-toluidine in a manner similar to that used for the preparation of 3-chloro-6-ethyl-2,4-dinitrobenzyl methyl ether. The crude product after recrystallization from methanol had m.p. 79.5°–81°.

In a manner similar to Examples 5 and 11 the appropriate 2,6-dinitrochloro intermediate is allowed to react in hot toluene with the appropriate methoxy amine to give the following compounds.

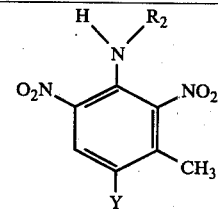

| Ex | $R_2$ | Y | MP° C. |
|---|---|---|---|
| 30 | $CH(CH_3)CH_2OCH_3$ | Cl | 43–45 |
| 31 | $CH(C_2H_5)CH_2OCH_3$ | $C_2H_5$ | 56.5–58.5 |
| 32 | $CH(C_2H_5)CH_2OCH_3$ | $C_3H_7$-n | 53 |

The selective preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous-acetone solution containing test compound in sufficient quantity to provide the equivalent of about 0.06 to 10 pounds per acre of test compound per cup. The treated cups are then placed on greenhouse benches, watered and cared for in accordance with conventional greenhouse procedures. Three or four weeks after treatment, the tests are terminated and each cup is examined and rated according to the rating system set forth below. The herbicidal proficiency of the active ingredients of the present invention is evident from the test results which are reported in the tables below.

| Rating System | |
|---|---|
| Rating System | % Difference in Growth from the check* |
| 0 - no effect | 0 |
| 1 - possible effect | 1–10 |
| 2 - slight effect | 11–25 |
| 3 - moderate effect | 26–40 |
| 5 - definite injury | 41–60 |
| 6 - herbicidal effect | 61–75 |
| 7 - good herbicidal effect | 76–90 |
| 8 - approaching complete kill | 91–99 |
| 9 - complete kill | 100 |
| 4 - abnormal growth, i.e., a definite physiological malformation but with an over-all effect less than a 5 on the rating scale. | |

*Based on visual determination of stand, size, vigor, chlorosis, growth malformation and over-all plant appearance.

| Plant Abbreviations | |
|---|---|
| CR - Crabgrass | BA - Barnyard grass |
| VEL - Velvet leaf | FOX - Green foxtail |
| PI - Pigweed | MG - Annual Morning-glory |

| Plant Abbreviations | | Plant Abbreviations | |
|---|---|---|---|
| LA - Lambsquarters | COT - Cotton | MU - Mustard | |
| COR - Corn | SB - Sugarbeets | RA - Ragweed | |
| WO - Wild oats | SOY - Soybean | TW - Teaweed | |
| SE - Sesbania | | | |

TABLE V

Preemergence Herbicidal Evaluation of

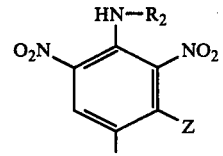

| Structure | | | Rate | Plant Species | | | | | | | |
|---|---|---|---|---|---|---|---|---|---|---|---|
| R₂ | Z | Y | l/Acre | SE | MU | PI | RG | MG | TW | VL | BA |
| ****CH(CH₃)CH₂OCH₃ | CH₃ | CH₃ | 10.0 | | 9 | 9 | 9 | 8 | 9 | 9 | 9 |
| | | | 4.0 | | 9 | 9 | | 5 | | 7 | 9 |
| | | | 2.0 | | 8.5 | 3 | | | | 6 | 8.5 |
| | | | 1.0 | | 7 | 0 | | | | 4 | 8.5 |
| | | | 0.50 | | 6.5 | 0 | | | | 1 | 7.5 |
| | | | 0.25 | | 5.5 | 0 | | | | 0 | 6.5 |
| | | | 0.13 | | 0 | 0 | | | | 0 | 3 |
| *****CH(C₂H₅)CH₂OCH₃ | CH₃ | CH₃ | 10.0 | | 8 | 9 | 9 | 8 | 8 | 8 | 9 |
| | | | 4.0 | | | 9 | | 7 | | 7 | 9 |
| | | | 2.0 | | | 8.2 | | 2.5 | | 7.2 | 9 |
| | | | 1.0 | | | 7.5 | | 0.5 | | 3 | 8.5 |
| | | | 0.50 | | | 5.5 | | 0 | | 0 | 7 |
| | | | 0.25 | | | 2.5 | | 0 | | 0 | 5.2 |
| | | | 0.13 | | | 1 | | 0 | | 0 | 2.2 |
| | | | 0.06 | | | 0 | | 0 | | 0 | 0 |
| CH(C₂H₅)CH₂OCH₃ (+) | CH₃ | CH₃ | 10.0 | | 8 | 9 | 3 | 8 | 8 | 8 | 9 |
| | | | 4.0 | | | 8 | | 6 | | 6 | 9 |
| | | | 2.0 | | | 7 | | 0 | | 5 | 9 |
| | | | 1.0 | | | 3 | | 0 | | 0 | 7 |
| | | | 0.50 | | | 1 | | 0 | | 0 | 5 |
| | | | 0.25 | | | 0 | | 0 | | 0 | 0 |
| | | | 0.13 | | | 0 | | 0 | | 0 | 0 |
| CH(C₂H₅)CH₂OCH₃ (−) | CH₃ | CH₃ | 10.0 | | 9 | 9 | 9 | 8 | 8 | 8 | 9 |
| | | | 4.0 | | | 9 | | 8 | | 8 | 9 |
| | | | 2.0 | | | 9 | | 6 | | 8 | 9 |
| | | | 1.0 | | | 8 | | 3 | | 7 | 9 |
| | | | 0.50 | | | 7 | | 0 | | 2 | 8 |
| | | | 0.25 | | | 3 | | 0 | | 0 | 6 |
| | | | 0.13 | | | 1 | | 0 | | 0 | 2 |
| | | | 0.06 | | | 0 | | 0 | | 0 | 8 |
| CH(CH₃)CH₂OCH₃ | CH₂OCH₃ | CH₃ | 10.0 | 8 | 9 | 9 | 9 | 8 | 8 | 8 | 9 |
| | | | 1.0 | 6 | 3 | 7 | 0 | 1 | 7 | 6 | 9 |
| | | | 0.50 | 2 | 0 | 7 | 0 | 0 | 6 | 3 | 9 |
| | | | 0.25 | 2 | 0 | 6 | 0 | 0 | 5 | 1 | 7 |
| | | | 0.13 | 0 | 0 | 1 | 0 | 0 | 3 | 1 | 6 |
| | | | 0.06 | 0 | 0 | 0 | 0 | 0 | 1 | 0 | 1 |
| | | | 0.03 | 0 | 0 | 0 | 0 | 0 | 1 | 0 | 0 |
| CH(CH₃)CH₂OCH₃ | CH₂OCH₃ | C₂H₅ | 10.0 | 8 | 9 | 9 | 9 | 9 | 9 | 9 | 9 |
| | | | 1.0 | 2 | 9 | 9 | 0 | 8 | 9 | 8 | 9 |
| | | | 0.50 | 0 | 2 | 9 | 0 | 0 | 8 | 7 | 9 |
| | | | 0.25 | 0 | | 9 | 0 | 0 | 3 | 3 | 9 |
| | | | 0.13 | 0 | 0 | 2 | 0 | 0 | 2 | 0 | 8 |
| | | | 0.06 | 0 | 0 | 2 | 0 | 0 | 0 | 0 | 6 |
| | | | 0.03 | 0 | 0 | 0 | 0 | 0 | 0 | 0 | 2 |
| CH(CH₃)CH₂CH₂OCH₃ | CH₂OCH₃ | Cl | 10.0 | 0 | 8 | 9 | 0 | 8 | 8 | 7 | 9 |
| | | | 1.0 | 9 | 0 | 0 | 0 | 0 | 0 | 2 | 5 |
| | | | 0.50 | 0 | 0 | 0 | 0 | 0 | 0 | 0 | 2 |
| | | | 0.25 | 0 | 0 | 0 | 0 | 0 | 0 | 0 | 0 |
| CH(C₂H₅)CH₂OCH₃ | CH₂OCH₃ | C₂H₅ | 10.0 | 9 | 9 | 9 | 9 | 9 | 9 | 9 | 9 |
| | | | 1.0 | 7 | 8 | 9 | 0 | 2 | 9 | 9 | 9 |
| | | | 0.50 | 6 | 9 | 9 | 0 | 0 | 8 | 8 | 9 |
| | | | 0.25 | 2 | 9 | 9 | 0 | 0 | 7 | 6 | 9 |
| | | | 0.13 | 0 | 3 | 7 | 0 | 0 | 3 | 3 | 9 |
| | | | 0.06 | 0 | 0 | 6 | 0 | 0 | 0 | 2 | 9 |
| | | | 0.03 | 0 | | 5 | 0 | 0 | 0 | 0 | 9 |
| CH(C₂H₅)CH₂OCH₃ | CH₂OCH₃ | CH₃ | 10.0 | 9 | 9 | 9 | 9 | 8 | 9 | 9 | 9 |
| | | | 1.0 | 0 | 9 | 9 | 0 | 2 | 9 | 8 | 9 |
| | | | 0.50 | 0 | 8 | 9 | 0 | 0 | 8 | 8 | 9 |
| | | | 0.25 | 0 | 0 | 7 | 0 | 0 | 2 | 2 | 9 |
| | | | 0.13 | 0 | 0 | 5 | 0 | 0 | 0 | 0 | 9 |
| | | | 0.06 | 0 | 0 | 0 | 0 | 0 | 0 | 0 | 8 |
| | | | 0.03 | 0 | 0 | 0 | 0 | 0 | 0 | 0 | 2 |
| CH(CH₃)CH₂OCH₃ | CH₂OCH₃ | C₃H₇-i | 10.0 | 9 | 9 | 9 | 9 | 8 | 9 | 8 | 9 |
| | | | 1.0 | 6 | 9 | 9 | 7 | 7 | 7 | 8 | 9 |
| | | | 0.50 | 6 | 9 | 9 | 0 | 0 | 8 | 6 | 9 |
| | | | 0.25 | | 9 | 8 | 0 | 0 | 6 | 5 | 9 |
| | | | 0.13 | 0 | 5 | 6 | 0 | 0 | 0 | 2 | 9 |
| | | | 0.06 | 0 | | 2 | 0 | 0 | | 0 | 9 |
| | | | 0.03 | 0 | | 0 | 0 | 0 | 0 | 0 | 0 |
| CH(CH₃)CH₂CH₂OCH₃ | CH₂OCH₃ | C₃H₇-i | 10.0 | 9 | 9 | 9 | 9 | 8 | 9 | 8 | 9 |
| | | | 1.0 | 0 | 9 | 9 | 0 | 0 | 7 | 3 | 9 |
| | | | 0.50 | 0 | 9 | 9 | 0 | 0 | 2 | 2 | 9 |

TABLE V-continued
Preemergence Herbicidal Evaluation of

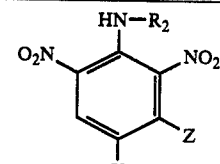

| R₂ | Z | Y | Rate lb/Acre | | | | | | | |
|---|---|---|---|---|---|---|---|---|---|---|
| | | | 0.25 | 0 | 8 | 7 | 0 | 0 | 0 | 0 | 9 |
| | | | 0.13 | 0 | 8 | 2 | 0 | 0 | 0 | 0 | 9 |
| | | | 0.06 | 0 | | 0 | 0 | 0 | 0 | 0 | 8 |
| | | | 0.03 | 0 | | 0 | 0 | 0 | 0 | 0 | 3 |
| CH(CH₃)CH₂OCH₃ | CH₂OCH₃ | Cl | 10.0 | 8 | 9 | 9 | 8 | 8 | 8 | 8 | 9 |
| | | | 1.0 | 0 | | 7 | 0 | 0 | 8 | 0 | 9 |
| | | | 0.50 | 0 | 0 | 0 | 0 | 0 | 0 | | 9 |
| | | | 0.25 | 0 | | 0 | 0 | 0 | 0 | 0 | 3 |
| | | | 0.13 | 0 | | 0 | 0 | 0 | 0 | 0 | 2 |
| | | | 0.06 | 0 | 0 | 0 | 0 | 0 | 0 | 0 | 0 |
| | | | 0.03 | 0 | | 0 | 0 | 0 | 0 | 0 | 0 |
| CH(C₂H₅)CH₂OCH₃ | CH₂OCH₃ | C₃H₇-i | 10.0 | 8 | 9 | 9 | 9 | 8 | 8 | 8 | 9 |
| | | | 1.0 | 8 | 9 | 9 | 3 | 1 | 8 | 6 | 9 |
| | | | 0.50 | 5 | 9 | 9 | 3 | 1 | 8 | 5 | 9 |
| | | | 0.25 | 5 | 0 | 8 | 0 | 1 | 7 | 3 | 9 |
| | | | 0.13 | 0 | | 8 | 0 | 0 | 5 | 2 | 9 |
| | | | 0.06 | 0 | 0 | 7 | 0 | 0 | 2 | 0 | 9 |
| | | | 0.03 | 0 | 0 | 2 | 0 | 0 | 0 | 0 | 9 |
| CH(CH₃)CH₂OCH₃ | CH₃ | Cl | 10.0 | | 9 | 9 | 6 | 8 | 9 | 8 | 9 |
| CH(C₂H₅)CH₂OCH₃ | CH₃ | Cl | 10.0 | | 8 | 8 | 0 | 8 | 8 | 8 | 9 |
| | | | 4.0 | | | 8 | | 7 | | 7 | 9 |
| | | | 2.0 | | | 7 | | 5 | | 5 | 9 |
| | | | 1.0 | | | 5 | | 0 | | 5 | 8 |
| | | | 0.50 | | | 3 | | 0 | | 3 | 6 |
| | | | 0.25 | | | 0 | | 0 | | 0 | 3 |
| CH(C₂H₅)CH₂OCH₃ | CH₃ | Cl | 10.0 | | 8 | 9 | 0 | 8 | 8 | 8 | 9 |
| | | | 4.0 | | | 9 | | 5 | | 6 | 9 |
| | | | 2.0 | | | 8 | | 5 | | 5 | 9 |
| | | | 1.0 | | | 7 | | 0 | | 0 | 8 |
| | | | 0.50 | | | 6 | | 0 | | 0 | 7 |
| | | | 0.25 | | | 1 | | 0 | | 0 | 3 |

| Structure | | | Rate | Plant Species | | | | | | | |
|---|---|---|---|---|---|---|---|---|---|---|---|
| R₂ | Z | Y | lb/Acre | CR | GF | WO | CN | CO | SY | SB | RI |
| ****CH(CH₃)CH₂OCH₃ | CH₃ | CH₃ | 10.0 | 9 | 9 | 0 | | | | | |
| | | | 4.0 | 9 | 9 | 5 | 0 | 0 | 5 | 8 | |
| | | | 2.0 | 9 | 9 | 0 | 0 | 0 | 0 | 7 | |
| | | | 1.0 | 9 | 7.5 | 0 | 0 | 0 | 0 | 5.5 | |
| | | | 0.50 | 8 | 4.5 | 0 | 0 | 0 | 0 | 3.5 | |
| | | | 0.25 | 7 | 2.5 | 0 | 0 | 0 | 0 | 2 | |
| | | | 0.13 | 8 | 5 | 0 | 0 | 0 | 0 | 0 | |
| *****CH(C₂H₅)CH₂OCH₃ | CH₃ | CH₃ | 10.0 | 9 | 9 | 6 | | | | | |
| | | | 4.0 | 9 | 9 | 5 | | | | | |
| | | | 2.0 | 9 | 9 | 1.5 | 0.7 | 0.7 | 0 | 7 | |
| | | | 1.0 | 9 | 9 | 0.2 | 0 | 0 | 0 | 4 | |
| | | | 0.50 | 9 | 8.2 | 0 | 0 | 0 | 0 | 0.7 | |
| | | | 0.25 | 9 | 7.2 | 0 | 0 | 0 | 0 | 0.7 | |
| | | | 0.13 | 7 | 4.7 | 0 | 0 | 0 | 0 | 0 | |
| | | | 0.06 | 1 | 3 | 0 | 0 | 0 | 0 | 0 | |
| CH(C₂H₅)CH₂OCH₃ (+) | CH₃ | CH₃ | 10.0 | 9 | 9 | 6 | | | | | |
| | | | 4.0 | 9 | 9 | 0 | 0 | 0 | 0 | 7 | |
| | | | 2.0 | 9 | 8 | 0 | 0 | 0 | 0 | 6 | |
| | | | 1.0 | 8 | 7 | 0 | 0 | 0 | 0 | 2 | |
| | | | 0.50 | 7 | 5 | 0 | 0 | 0 | 0 | 0 | |
| | | | 0.25 | 1 | 0 | 0 | 0 | 0 | 0 | 0 | |
| | | | 0.13 | 0 | 0 | 0 | 0 | 0 | 0 | 0 | |
| CH(C₂H₅)CH₂OCH₃ (−) | CH₃ | CH₃ | 10.0 | 9 | 9 | 6 | | | | | |
| | | | 4.0 | 9 | 9 | 0 | 5 | 0 | | 8 | |
| | | | 2.0 | 9 | 9 | 0 | 5 | 0 | 2 | 8 | |
| | | | 1.0 | 9 | 9 | 0 | 0 | 0 | 0 | 6 | |
| | | | 0.50 | 9 | 9 | 0 | 0 | 0 | 0 | 0 | |
| | | | 0.25 | 9 | 7 | 0 | 0 | 0 | 0 | 0 | |
| | | | 0.13 | 9 | 3 | 0 | 0 | 0 | 0 | 0 | |
| | | | 0.06 | 1 | 0 | 0 | 0 | 0 | 0 | 0 | |
| CH(CH₃)CH₂OCH₃ | CH₂OCH₃ | CH₃ | 10.0 | 9 | 9 | 8 | | | | | |
| | | | 1.0 | 9 | 9 | 2 | 1 | 0 | | | |
| | | | 0.50 | 9 | 9 | 1 | 0 | 0 | 0 | | |
| | | | 0.25 | 7 | 6 | 0 | 0 | 0 | 0 | | |
| | | | 0.13 | 7 | 7 | 0 | 0 | 0 | 0 | | |
| | | | 0.06 | 6 | 6 | 0 | 0 | | | | |
| | | | 0.03 | 2 | 2 | 0 | 0 | 0 | | | |
| CH(CH₃)CH₂OCH₃ | CH₂OCH₃ | C₂H₅ | 10.0 | 9 | 9 | 9 | | | | | |
| | | | 1.0 | 9 | 9 | 0 | 0 | 0 | 0 | | |
| | | | 0.50 | 9 | 9 | 0 | 0 | 0 | 0 | | |
| | | | 0.25 | 9 | 9 | 0 | 0 | 0 | 0 | | |
| | | | 0.13 | 9 | 9 | 0 | 0 | 0 | 0 | | |
| | | | 0.06 | 9 | 9 | 0 | 0 | 0 | 0 | | |
| | | | 0.03 | 6 | 6 | 0 | 0 | 0 | | | |
| CH(CH₃)CH₂CH₂OCH₃ | CH₂OCH₃ | Cl | 10.0 | 9 | 9 | 3 | | | | | |
| | | | 1.0 | 9 | 7 | 0 | 0 | 0 | 0 | | |
| | | | 0.50 | 6 | 6 | 0 | 0 | 0 | 0 | | |
| | | | 0.25 | 0 | 0 | 0 | 0 | 0 | 0 | | |
| CH(C₂H₅)CH₂OCH₃ | CH₂OCH₃ | C₂H₅ | 10.0 | 9 | 9 | 8 | | | | | |

TABLE V-continued

Preemergence Herbicidal Evaluation of $$\begin{array}{c} HN-R_2 \\ O_2N \diagup \diagdown NO_2 \\ | \quad | \\ \diagdown \diagup Z \\ Y \end{array}$$

| $R_1$ | $R_2$ | Z | Rate | | | | | | | |
|---|---|---|---|---|---|---|---|---|---|---|
| CH(C₂H₅)CH₂OCH₃ | CH₂OCH₃ | CH₃ | 1.0 | 9 | 9 | 5 | 5 | 7 | 0 | |
| | | | 0.50 | 9 | 9 | 2 | 8 | 0 | 0 | |
| | | | 0.25 | 9 | 9 | 0 | 0 | 0 | 0 | |
| | | | 0.13 | 9 | 9 | 0 | 0 | 0 | 0 | |
| | | | 0.06 | 9 | 9 | 0 | 0 | 0 | 0 | |
| | | | 0.03 | 9 | 9 | 0 | 0 | 0 | 0 | |
| CH(CH₃)CH₂OCH₃ | CH₂OCH₃ | C₃H₇-i | 10.0 | 9 | 9 | 9 | | | | |
| | | | 1.0 | 9 | 9 | 2 | 7 | 0 | 2 | |
| | | | 0.50 | 9 | 9 | 0 | 3 | 0 | 0 | |
| | | | 0.25 | 9 | 9 | 0 | 2 | 0 | | |
| | | | 0.13 | 9 | 8 | 0 | 2 | 0 | 0 | |
| | | | 0.06 | 9 | 7 | 0 | 0 | 0 | 0 | |
| | | | 0.03 | 2 | 0 | 0 | 0 | 0 | 0 | |
| CH(CH₃)CH₂CH₂OCH₃ | CH₂OCH₃ | C₃H₇-i | 10.0 | 9 | 9 | 9 | | | | |
| | | | 1.0 | 9 | 9 | 2 | 6 | 0 | 2 | |
| | | | 0.50 | 9 | 9 | 2 | 0 | 0 | 2 | |
| | | | 0.25 | 9 | 9 | 0 | 0 | 0 | 0 | |
| | | | 0.13 | 9 | 9 | 0 | 0 | 0 | 0 | |
| | | | 0.06 | 9 | 9 | 0 | 0 | 0 | 0 | |
| | | | 0.03 | 9 | 9 | 0 | 0 | 0 | 0 | |
| CH(CH₃)CH₂OCH₃ | CH₂OCH₃ | Cl | 10.0 | 9 | 9 | 9 | | | | |
| | | | 1.0 | 9 | 9 | 0 | 6 | 0 | 0 | |
| | | | 0.50 | 9 | 9 | 0 | 3 | 0 | 0 | |
| | | | 0.25 | 9 | 9 | 0 | 0 | 0 | 0 | |
| | | | 0.13 | 9 | 9 | 0 | 0 | 0 | 0 | |
| | | | 0.06 | 9 | 6 | 0 | 0 | 0 | 0 | |
| | | | 0.03 | 8 | 3 | 0 | 0 | 0 | 0 | |
| CH(C₂H₃)CH₂OCH₃ | CH₂OCH₃ | C₃H₇-i | 10.0 | 9 | 9 | 9 | | | | |
| | | | 1.0 | 9 | 9 | 0 | 0 | 0 | 0 | |
| | | | 0.50 | 9 | 9 | 0 | 0 | 0 | 0 | |
| | | | 0.25 | 9 | 8 | 0 | 0 | 0 | 0 | |
| | | | 0.13 | 6 | 0 | 0 | 0 | 0 | 0 | |
| | | | 0.06 | 3 | 0 | 0 | 0 | 0 | 0 | |
| | | | 0.03 | 0 | 0 | 0 | 0 | 0 | 0 | |
| CH(C₂H₃)CH₂OCH₃ | CH₂OCH₃ | C₃H₇-i | 10.0 | 9 | 9 | | | | | |
| | | | 1.0 | 9 | 9 | | 5 | 0 | 0 | 0 |
| | | | 0.50 | 9 | 9 | | 8 | 0 | 0 | 0 |
| | | | 0.25 | 9 | 9 | | 3 | 0 | 0 | 0 |
| | | | 0.13 | 9 | 9 | | 1 | 0 | 0 | 0 |
| | | | 0.06 | 9 | 9 | | 0 | 0 | 0 | 0 |
| | | | 0.03 | 9 | 9 | | 0 | 0 | 0 | 0 |
| CH(CH₃)CH₂OCH₃ | CH₃ | Cl | 10.0 | 9 | 9 | 9 | | | | |
| CH(C₂H₅)CH₂OCH₃ | CH₃ | Cl | 10.0 | 9 | 9 | 2 | | | | |
| | | | 4.0 | 9 | 9 | 5 | 1 | 1 | 5 | 6 |
| | | | 2.0 | 9 | 9 | 1 | 0 | 0 | 3 | 5 |
| | | | 1.0 | 9 | 9 | 0 | 0 | 0 | 0 | 3 |
| | | | 0.50 | 8 | 6 | 0 | 0 | 0 | 0 | 3 |
| | | | 0.25 | 5 | 3 | 0 | 0 | 0 | 0 | 1 |
| CH(C₂H₅)CH₂OCH₃ (−) | CH₃ | Cl | 10.0 | 9 | 9 | 5 | | | | |
| | | | 4.0 | 9 | 9 | 5 | 6 | 5 | 6 | 8 |
| | | | 2.0 | 9 | 9 | 3 | 1 | 0 | 1 | 7 |
| | | | 1.0 | 9 | 8 | 3 | 0 | 0 | 0 | 5 |
| | | | 0.50 | 9 | 8 | 0 | 0 | 0 | 0 | 1 |
| | | | 0.25 | 8 | 6 | 0 | 0 | 0 | 0 | 0 |

****Average of 1 to 2 tests
*****Averaged 1 to 4 tests

From the data reported in the table below, it can be seen that (1) the racemic compounds are highly active herbicidal agents; (2) the dextrorotatory (+) isomers are less active than the racemic compounds, but still effective as herbicidal agents at higher rates of application; and (3) the levorotatory (−) isomers are much more effective as herbicidal agents than either the corresponding racemic compound or the corresponding dextrorotatory (+) isomer.

TABLE VI

Herbicidal Activity of Optically Active and Racemic Dinitroaniline Compounds

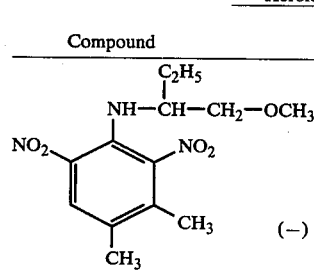

| Compound | Rate lb./Acre | LA | PI | MG | BA | CR | FO | WO | CN | CO | SY | SB | VL |
|---|---|---|---|---|---|---|---|---|---|---|---|---|---|
| | 4 | 8 | 9 | 8 | 9 | 9 | 9 | 0 | 5 | 0 | — | 8 | 8 |
| | 2 | 8 | 9 | 6 | 9 | 9 | 9 | 0 | 5 | 0 | 2 | 8 | 8 |
| | 1 | 8 | 8 | 3 | 9 | 9 | 9 | 0 | 0 | 0 | 0 | 6 | 7 |
| | 1/2 | 8 | 7 | 0 | 8 | 9 | 9 | 0 | 0 | 0 | 0 | 0 | 2 |
| | 1/4 | 7 | 3 | 0 | 6 | 9 | 7 | 0 | 0 | 0 | 0 | 0 | 0 |
| | 1/8 | 5 | 1 | 0 | 2 | 9 | 3 | 0 | 0 | 0 | 0 | 0 | 0 |
| | 1/16 | 0 | 0 | 0 | 0 | 8 | 1 | 0 | 0 | 0 | 0 | 0 | 0 |

TABLE VI-continued
Herbicidal Activity of Optically Active and Racemic Dinitroaniline Compounds

| Compound | Rate lb./Acre | LA | PI | MG | BA | CR | FO | WO | CN | CO | SY | SB | VL |
|---|---|---|---|---|---|---|---|---|---|---|---|---|---|
| (structure, ±) | 2 | 8 | 8 | 0 | 9 | 9 | 9 | 0 | 0 | 0 | 0 | 8 | 7 |
| | 1 | 8 | 8 | 0 | 7 | 9 | 9 | 0 | 0 | 0 | 0 | 0 | 0 |
| | 1/2 | 8 | 6 | 0 | 5 | 9 | 8 | 0 | 0 | 0 | 0 | 0 | 0 |
| | 1/4 | 7 | 0 | 0 | 0 | 9 | 5 | 0 | 0 | 0 | 0 | 0 | 0 |
| | 1/8 | 2 | 0 | 0 | 0 | 6 | 2 | 0 | 0 | 0 | 0 | 0 | 0 |
| | 1/16 | 0 | 0 | 0 | 0 | 1 | 3 | 0 | 0 | 0 | 0 | 0 | 0 |
| (structure, +) | 4 | 8 | 8 | 6 | 9 | 9 | 9 | 0 | 0 | 0 | 0 | 7 | 6 |
| | 2 | 8 | 7 | 0 | 9 | 9 | 8 | 0 | 0 | 0 | 0 | 6 | 5 |
| | 1 | 8 | 3 | 0 | 7 | 8 | 7 | 0 | 0 | 0 | 0 | 2 | 0 |
| | 1/2 | 7 | 1 | 0 | 5 | 7 | 5 | 0 | 0 | 0 | 0 | 0 | 0 |
| | 1/4 | 2 | 0 | 0 | 0 | 1 | 0 | 0 | 0 | 0 | 0 | 0 | 0 |
| | 1/8 | 0 | 0 | 0 | 0 | 0 | 0 | 0 | 0 | 0 | 0 | 0 | 0 |
| | 1/16 | 0 | 0 | 0 | 0 | 0 | 0 | 0 | 0 | 0 | 0 | 0 | 0 |

We claim:

1. A compound of the formula:

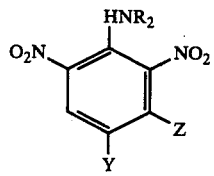

wherein

Y is $CH_3$, $C_2H_5$, i-$C_3H_7$, n-$C_3H_7$, i-$C_4H_9$, sec-$C_4H_9$, or Cl $R_2$ is secondary $C_3$-$C_4$ alkyl monosubstituted with methoxy and Z is $CH_3$ or —$CH_2OCH_3$.

2. A compound according to claim 1: $\alpha^3$-Methoxy-N[1-(methoxymethyl)propyl]-2,6-dinitro-3,4-xylidine.

3. A compound according to claim 1: N-[1-(methoxymethyl)propyl]-2,6-dinitro-3,4-xylidine.

4. A compound according to claim 1: 4-chloro-N-[1-methoxymethyl)propyl]-2,6-dinitro-m-toluidine.

5. A compound according to claim 1: N-[1-(methoxymethyl)ethyl]-2,6-dinitro-3,4-xylidine.

6. A compound according to claim 1: (+)-N-[1-(methoxymethyl)propyl]-2,6-dinitro-3,4-xylidine.

7. A compound according to claim 1: (−)-N-[1-(methoxymethyl)propyl]-2,6-dinitro-3,4-xylidine.

8. A compound according to claim 1: (−)-4-chloro-N-[1-methoxymethyl)propyl]-2,6-dinitro-m-toluidine.

9. A compound according to claim 1: $\alpha^3$-methoxy-N-(2-methoxy-1-methylethyl)-2,6-dinitro-3,4-xylidine.

10. A compound according to claim 1: 4-ethyl-$\alpha$-methoxy-N-(2-methoxy-1-methylethyl)-2,6-dinitro-m-toluidine.

11. A compound according to claim 1: 4-chloro-$\alpha$-methoxy-N-(3-methoxy-1-methylpropyl)-2,6-dinitro-m-toluidine.

12. A compound according to claim 1: 4-ethyl-$\alpha$-methoxy-N-[1-(methoxymethyl)propyl]-2,6-dinitro-m-toluidine.

13. A compound according to claim 1: $\alpha^3$-Methoxy-N[1-(methoxymethyl)propyl]-2,6-dinitro-3,4-xylidine.

14. A compound according to claim 1: 7-methoxy-N-(3-methoxy-1-methylpropyl)-4,6-dinitro-o-cymen-5-amine.

15. A compound according to claim 1: 4-chloro-$\alpha$-methoxy-N-(2-methoxy-1-methylethyl)-2,6-dinitro-m-toluidine.

16. A compound according to claim 1: 7-methoxy-N-[1-(methoxymethyl)propyl]-4,6-dinitro-o-cymen-5-amine.

17. A compound according to claim 1: 4-chloro-N-(2-methoxy-1-methylethyl)-2,6-dinitro-m-toluidine.

18. A compound according to claim 1: 7-methoxy-N-(2-methoxy-1-methylethyl)-4,6-dinitro-o-cymen-5-amine.

* * * * *